US010111946B2

(12) United States Patent
Steigerwald et al.

(10) Patent No.: US 10,111,946 B2
(45) Date of Patent: Oct. 30, 2018

(54) POXVIRAL VECTORS FOR LOW ANTIBODY RESPONSE AFTER A FIRST PRIMING IMMUNIZATION

(71) Applicant: Bavarian Nordic A/S, Kvistgaard (DK)

(72) Inventors: Robin Steigerwald, Munich (DE); Kay Brinkmann, Munich (DE); Ulrike Dirmeier, Starnberg (DE); Paul Chaplin, Grafelfing (DE)

(73) Assignee: BAVARIAN NORDIC A/S, Kvistgaard (DK)

( * ) Notice: Subject to any disclaimer, the term of this patent is extended or adjusted under 35 U.S.C. 154(b) by 70 days.

(21) Appl. No.: 14/409,309

(22) PCT Filed: Jun. 21, 2013

(86) PCT No.: PCT/EP2013/001849
§ 371 (c)(1),
(2) Date: Dec. 18, 2014

(87) PCT Pub. No.: WO2013/189611
PCT Pub. Date: Dec. 27, 2013

(65) Prior Publication Data
US 2015/0174238 A1 Jun. 25, 2015

Related U.S. Application Data

(60) Provisional application No. 61/663,238, filed on Jun. 22, 2012.

(30) Foreign Application Priority Data

Nov. 14, 2012 (EP) .................................. 12 007 729

(51) Int. Cl.
| | | |
|---|---|---|
| A61K 39/285 | (2006.01) | |
| C12N 15/86 | (2006.01) | |
| C12N 7/00 | (2006.01) | |
| C12N 15/11 | (2006.01) | |
| A61K 39/00 | (2006.01) | |

(52) U.S. Cl.
CPC .............. *A61K 39/285* (2013.01); *C12N 7/00* (2013.01); *C12N 15/11* (2013.01); *C12N 15/86* (2013.01); *A61K 2039/53* (2013.01); *C12N 2710/24122* (2013.01); *C12N 2710/24134* (2013.01); *C12N 2710/24143* (2013.01); *C12N 2830/60* (2013.01)

(58) Field of Classification Search
CPC ...... C12N 2750/12022; C12N 2810/40; C12N 2810/60; C12N 2830/008; C12N 2840/203; C12N 2740/16062; C12N 2799/025; C12N 2799/027; C12N 2830/00; C12N 2710/24043; C12N 2799/023; C12N 15/86; C12N 2710/24143; C12N 2830/15; C07K 14/005; A61K 39/285; A61K 39/275
See application file for complete search history.

(56) References Cited

U.S. PATENT DOCUMENTS

| | | | | |
|---|---|---|---|---|
| 8,394,385 | B2* | 3/2013 | Hausmann ........... | A61K 39/285 424/199.1 |
| 8,613,936 | B2* | 12/2013 | Hausmann ........... | A61K 39/285 424/199.1 |
| 9,163,237 | B2* | 10/2015 | Hausmann ........... | A61K 39/285 |
| 2010/0233203 | A1* | 9/2010 | Hausmann ........... | A61K 39/285 424/199.1 |
| 2012/0014988 | A1* | 1/2012 | Hausmann ........... | A61K 39/285 424/199.1 |

FOREIGN PATENT DOCUMENTS

| WO | WO 2010/060632 A1 | 6/2010 |
|---|---|---|
| WO | WO 2010/102822 A1 | 9/2010 |

OTHER PUBLICATIONS

Funahashi et al. J. Virol. 1991, vol. 65 (10), pp. 5584-5588.*
Baur et al. J. Virol. 2010, vol. 84 (17), pp. 8743-8752.*
Davison et al. J. Mol. Biol, 1989, vol. 210, pp. 749-769.*
Bauer et al., Immediate-early expression of a recombinant antigen by modified vaccinia virus ankara breaks the immunodominance of strong vector-specific B8R antigen in acute and memory CD8 T-cell responses, Journal of Virology 84 (17), 8743-8752 (2010).
Garces et al., Reactivation of transcription from a vaccinia virus early promoter late in infection, Journal of Virology 67 (9), 5394-5401 (1993).
Davison et al., Structure of vaccinia virus late promoters, Journal of Molecular Biology 210 (4), 771-784 (1989).
Davison et al., Structure of vaccinia virus early promoters, Journal of Molecular Biology 210 (4), 749-769 (1989).
Hänggi et al., Conserved TAAAT motif in vaccinia virus late promoters: overlapping TATA box and site of transcription initiation, EMBO Journal 5 (5), 1071-1076 (1986).
Mars et al., Characterization of vaccinia virus early promoters and evaluation of their informational content, Journal of Molecular Biology 198 (4), 619-631 (1987).
Wennier et al., A novel naturally occurring tandem promoter in modified vaccinia virus ankara drives very early gene expression and potent immune responses, PLOS ONE 8 (8), e73511 (2013).

(Continued)

*Primary Examiner* — Bao Q Li

(57) ABSTRACT

The invention is drawn to compositions and methods for the induction of an immune response, in particular a strong CD8 T cell response, to a specific antigenic determinant without raising a significant antibody response to the antigenic determinant after a first, priming immunization. The method comprises administering to the host a recombinant poxviral vector comprising a transcriptional control element comprising an early and/or late element linked to a nucleotide sequence encoding the antigenic determinant. The recombinant poxviral vector comprises a transcriptional control element comprising an early and/or late element linked to a nucleotide sequence encoding the antigenic determinant. The late element may be stronger than the cowpox ATI promoter in HeLa cells.

17 Claims, 6 Drawing Sheets

Specification includes a Sequence Listing.

(56) References Cited

OTHER PUBLICATIONS

Yue et al., Evaluation of recombinant modified vaccinia Ankara virus-based rhesus cytomegalovirus vaccines in rhesus macaques, Medical Microbiology and Immunology 197 (2), 117-123 (2008).
International Search Report and Written Opinion of the International Search Authority for PCT/EP2013/001849 dated Oct. 25, 2013.
Extended European Search report for EP application 12007729.2, dated Jul. 31, 2013.
Wyatt et al., Development of a replication-deficient recombinant vaccinia virus vaccine effective against parainfluenza virus 3 infection in an animal model, Vaccine 14: 1451-1458 (1996).
Wyatt et al., Multiprotein HIV Type I Clade B DNA and MVA VAccines: Construction, Expression, and Immunogenicity in Rodents of the MVA component, AIDS Research and Human Retroviruses 20: 645-653 (2004).
Chakrabarti et al., Compact, Synthetic, Vaccinia Virus Early/Late Promoter for Protein Expression, BioTechniques 23:1094-1097 (1997).

* cited by examiner

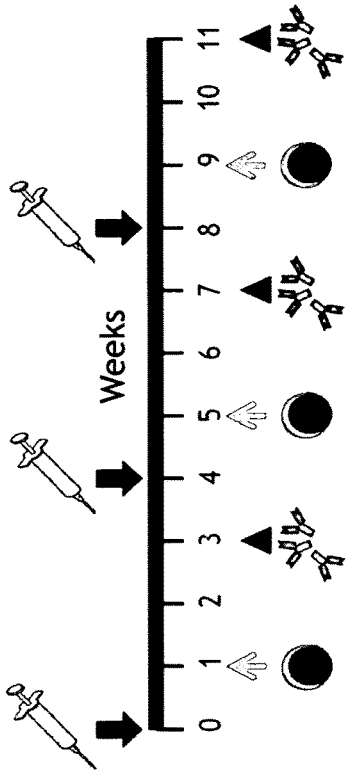
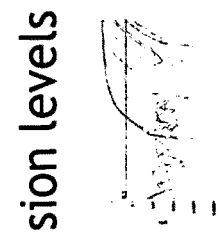
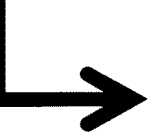
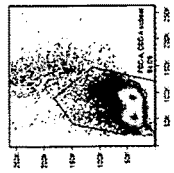
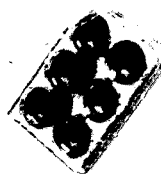
Figure 2

POXVIRAL VECTORS FOR LOW ANTIBODY RESPONSE AFTER A FIRST PRIMING IMMUNIZATION

This application is a National Phase application under 35 U.S.C. § 371 of International Application No. PCT/EP2013/001849, filed Jun. 21, 2013, and claims the benefit under 35 U.S.C. § 365 of European Application 12007729.2 filed Nov. 14, 2012, and the benefit under 35 U.S.C. § 119(e) of U.S. Provisional Patent Application 61/663,238 filed Jun. 22, 2012, the disclosures of which are incorporated by reference herein in their entirety.

BACKGROUND OF THE INVENTION

Recombinant viruses are widely used to express foreign antigens in infected cells. Replication-deficient recombinant viruses, such as replication deficient recombinant poxviruses are currently tested as promising vaccines to induce an immune response against a foreign antigen expressed from the poxvirus vector. Most popular are avipoxviruses on the one side and vaccinia viruses (VACV) on the other side. U.S. Pat. No. 5,736,368 and U.S. Pat. No. 6,051,410 disclose recombinant vaccinia virus strain Wyeth which expresses HIV antigens and proteins. U.S. Pat. No. 5,747,324 discloses a recombinant vaccinia virus strain NYCBH expressing lentivirus genes. EP 0 243 029 discloses a recombinant vaccinia virus strain Western Reserve expressing human retrovirus genes. For the expression of heterologous genes in pox viruses several promoters are known to the person skilled in the art, such as the 30K and 40K promoters (see e.g. U.S. Pat. No. 5,747,324), a strong synthetic early/late promoter (see e.g. Sutter et al., A recombinant vector derived from the host range-restricted and highly attenuated MVA strain of vaccinia virus stimulates protective immunity in mice to influenza virus, Vaccine 12, 1032-40, 1994), the P7.5 promoter (see e.g. Endo et al., Homotypic and heterotypic protection against influenza virus infection in mice by recombinant vaccinia virus expressing the haemagglutinin or nucleoprotein of influenza virus, J. Gen. Virol. 72,699-703, 1991) and the promoter derived from the cowpox virus A-type inclusion (ATI) gene (Li et al., High-level expression of *Amsacta moorei* entomopoxvirus spheroidin depends on sequences within the gene, J. Gen. Virol. 79, 613, 1998). All of these promoters have been used in recombinant vaccinia viruses to express heterologous genes and were shown to express said genes very efficiently resulting in relatively high amounts of the protein encoded by the heterologous gene. In general, for many vaccination approaches it is highly desired that the antigen against which an immune response is to be induced is expressed in high amounts.

Induction of a strong humoral and cellular immune response against a foreign gene product expressed by, e.g. a VACV vector is hampered by the fact that the foreign gene product has to compete with all of the more than 150 antigens of the VACV vector for recognition and induction of specific antibodies and T cells. The specific problem is the immunodominance of vector CD8 T cell epitopes which prevents induction of a strong CD8 T cell response against the foreign gene product. (Smith et al., Immunodominance of poxviral-specific CTL in a human trial of recombinant-modified vaccinia Ankara. J. Immunol. 175:8431-8437, 2005.) This applies to replicating VACV vectors such as Dryvax, as well as for non-replicating vectors like NYVAC and MVA.

For expression of a recombinant antigen by VACV, poxvirus-specific promoters but not common eukaryotic promoters may be used. The reason for this is the specific biology of poxviruses which replicate in the cytoplasm and bring their own, cell-autonomous transcriptional machinery with them that does not recognize typical eukaryotic promoters.

The viral replication cycle is divided into two major phases, an early phase comprising the first two hours after infection before DNA replication, and a late phase starting at the onset of viral DNA replication at 2-4 hours after infection. The late phase spans the rest of the viral replication cycle from ~2-20 h after infection until progeny virus is released from the infected cell. There are a number of poxviral promoter types which are distinguished and named by the time periods within the viral replication cycle in which they are active, for example, early and late promoters. (See, e.g., Davison and Moss, Structure of Vaccinia Virus Late Promoters, J. Mol. Biol. 210:771-784, 1989; Davison and Moss, Structure of Vaccinia Virus Early Promoters, J. Mol. Biol. 21 0:749-769, 1989; and Hirschmann et al., Mutational Analysis of a Vaccinia Virus Intermediate Promoter in vitro and in vivo, Journal of Virology 64:6063-6069, 1990, all of which are hereby incorporated by reference). Vaccinia virus p7.5 promoter was identified as belonging to immediate early promoters (WO 2010/102822). Immediate early promoters are sometimes also referred to as "Early 1.1" compared to "Early 1.2" being the early class of promoters. (Yang et al., Simultaneous high-resolution analysis of vaccinia virus and host cell transcriptomes by deep RNA sequencing, Proc. Natl. Acad. Sci. USA 107(25):11513-11518, 2010). Immediate early genes were defined as being expressed in the period spanning the first hour of the viral infection cycle. (Assarsson et al., Kinetic analysis of a complete poxvirus transcriptome reveals an immediate-early class of genes. Proc. Natl. Acad. Sci. U.S.A 105:2140-2145, 2008; Davison, A. J. and B. Moss. Structure of vaccinia virus early promoters. J. Mol. Biol. 21 0:749-769, 1989.). The p7.5 promoter is composed of a late and an early element and is derived from an immediate early gene.

Whereas early promoters can also be active late in infection, activity of late promoters is confined to the late phase. A third class of promoters, named intermediate promoters, is active at the transition of early to late phase and is dependent on viral DNA replication. The latter also applies to late promoters, however, transcription from intermediate promoters starts earlier than from typical late promoters and requires a different set of transcription factors.

It became increasingly clear over recent years that the choice of the temporal class of poxviral promoter for antigen expression has profound effects on the strength and quality of the antigen-specific immune response. It was shown years ago that T cell responses against antigens expressed under the control of a late promoter are weaker than those obtained with the same antigen under an early promoter. (Bronte et al., Antigen expression by dendritic cells correlates with the therapeutic effectiveness of a model recombinant poxvirus tumor vaccine. Proc. Natl. Acad. Sci. U.S. A 94:3183-3188, 1997, Coupar et al., Temporal regulation of influenza hemagglutinin expression in vaccinia virus recombinants and effects on the immune response. Eur. J. Immunol. 16:1479-1487, 1986.)

Even more strikingly, it was recently shown that in repeated autologous immunizations with VACV as well as with the replication-defective VACV vector MVA, recall CD8 T cell responses against antigens under an exclusively late promoter can fail completely. This failure resulted in an almost undetectable antigen-specific CD8 T cell response after the second immunization (Kastenmuller et al., Cross-competition of CD8+ T cells shapes the immunodominance hierarchy during boost vaccination, J. Exp. Med. 204:2187-2198, 2007).

Thus, early expression of antigens by VACV vectors appears to be crucial for efficient antigen-specific CD8 T cell responses. It has also been shown that an early-expressed VACV vector antigen not only competes with late expressed antigens but also with other early antigens for immunodominance in the CD8 T cell response (Kastenmuller et al., Cross-competition of CD8+ T cells shapes the immunodominance hierarchy during boost vaccination, J. Exp. Med. 204:2187-2198, 2007.) The specific properties of the early portion of the poxviral promoter might thus be very important for induction of an antigen-specific T cell response. Moreover, it is a commonly held view and a general rule that higher amounts of antigen are beneficial for induction of stronger antigen-specific immune responses (for the poxvirus field, see for example Wyatt et al., Correlation of immunogenicities and in vitro expression levels of recombinant modified vaccinia virus Ankara HIV vaccines. Vaccine 26:486-493, 2008).

A promoter combining 4 early promoter elements and a late promoter element from the ATI gene has been described previously (Funahashi et al., Increased expression in vivo and in vitro of foreign genes directed by A-type inclusion body hybrid promoters in recombinant vaccinia viruses. J. Virol. 65:5584-5588, 1991; Wyatt et al., Correlation of immunogenicities and in vitro expression levels of recombinant modified vaccinia virus Ankara HIV vaccines. Vaccine 26:486-493, 2008), and has been shown to direct increased early expression of antigen. However, T cell responses induced by a antigen driven by such a promoter in a recombinant replication-competent vaccinia virus vector have only been analyzed after a single immunization and were only slightly different from those obtained with the classical p7.5 promoter in this setting. (Funahashi et al., Increased expression in vivo and in vitro of foreign genes directed by A-type inclusion body hybrid promoters in recombinant vaccinia viruses. J. Virol. 65:5584-5588, 1991.)

Jin et al. (Constructions of vaccinia virus A-type inclusion body protein, tandemly repeated mutant 7.5 kDa protein, and hemagglutinin gene promoters support high levels of expression, Arch. Virol. 138:315-330, 1994) reported the construction of recombinant VACV harbouring promoters consisting of a VACV ATI promoter combined with tandem repeats (2 to 38 copies) of a mutated p7.5 promoter operably linked to the CAT gene. Up to 10 repetitions of the mutated p7.5 promoter were effective in increasing early gene expression. With all constructs, the amount of CAT protein produced in the presence of cytosine arabinoside (AraC) (i.e. when the viral replication cycle was arrested in the early phase) was less than one-tenth of the amount produced in the absence of AraC (Jin et al., Constructions of vaccinia virus A-type inclusion body protein, tandemly repeated mutant 7.5 kDa protein, and hemagglutinin gene promoters support high levels of expression, Arch. Virol. 138:315-330, 1994) indicating that although early gene expression was increased, most of the expressed antigen was obviously produced during the late phase of infection.

Recently, it was shown that repeated immunizations of mice with recombinant MVA expressing OVA under the control of a hybrid early-late promoter (pHyb) containing five copies of a strong early element led to superior acute and memory CD8 T-cell responses compared to those to Pr7.5- and PrS-driven OVA. Baur et al., Journal of Virology, Vol. 84 (17): 8743-8752 (2010). Moreover, OVA expressed under the control of pHyb replaced the MVA-derived B8R protein as the immunodominant CD8 T-cell antigen after three or more immunizations. Id.

In certain circumstances, the presence of antibodies against an antigen can lead to an antibody-dependent enhancement of the disease. See, e.g., Ubol et al., Clinical and Vaccine Immunology, Vol. 17 (12):1829-1835 (2010); Yoong, Virulence 1 (5): 409-413 (2010). Antibody-dependent enhancement (ADE) has, for example, been demonstrated in vitro for dengue viruses, as well as other enveloped viruses, and is considered to be an important mechanism in the pathogenesis of dengue hemorrhagic fever (DHF). While most cases of dengue fever (DF) are manifested after the first infection by any of the four serotypes, a large percentage of DHF cases occur in subjects who are infected for the second time by a serotype which is different from the first infecting serotype of dengue virus. These observations give rise to the hypothesis that sequential infection of an individual with antibody against one dengue serotype by a different virus serotype at an appropriate interval may result in DHF in a certain number of cases.

Thus, in such circumstances, it can be desirable to minimize the antibody response against the antigen.

BRIEF DESCRIPTION OF THE DRAWINGS

FIG. 2 depicts characterization of recombinant MVA-BN constructs. The levels of mRNA and OVA protein induced in human cells by the different promoters were compared in vitro, using RT-qPCR and flow cytometry based assays. The humoral and cellular immune responses induced by the promoters were compared in mice. The schedule of vaccinations and bleeds for analysis of immune responses is shown. Mice received a total of three immunizations spaced 4 weeks apart. T cell responses and antibody responses were analyzed one week and three weeks after each vaccination, respectively.

Figure 1:
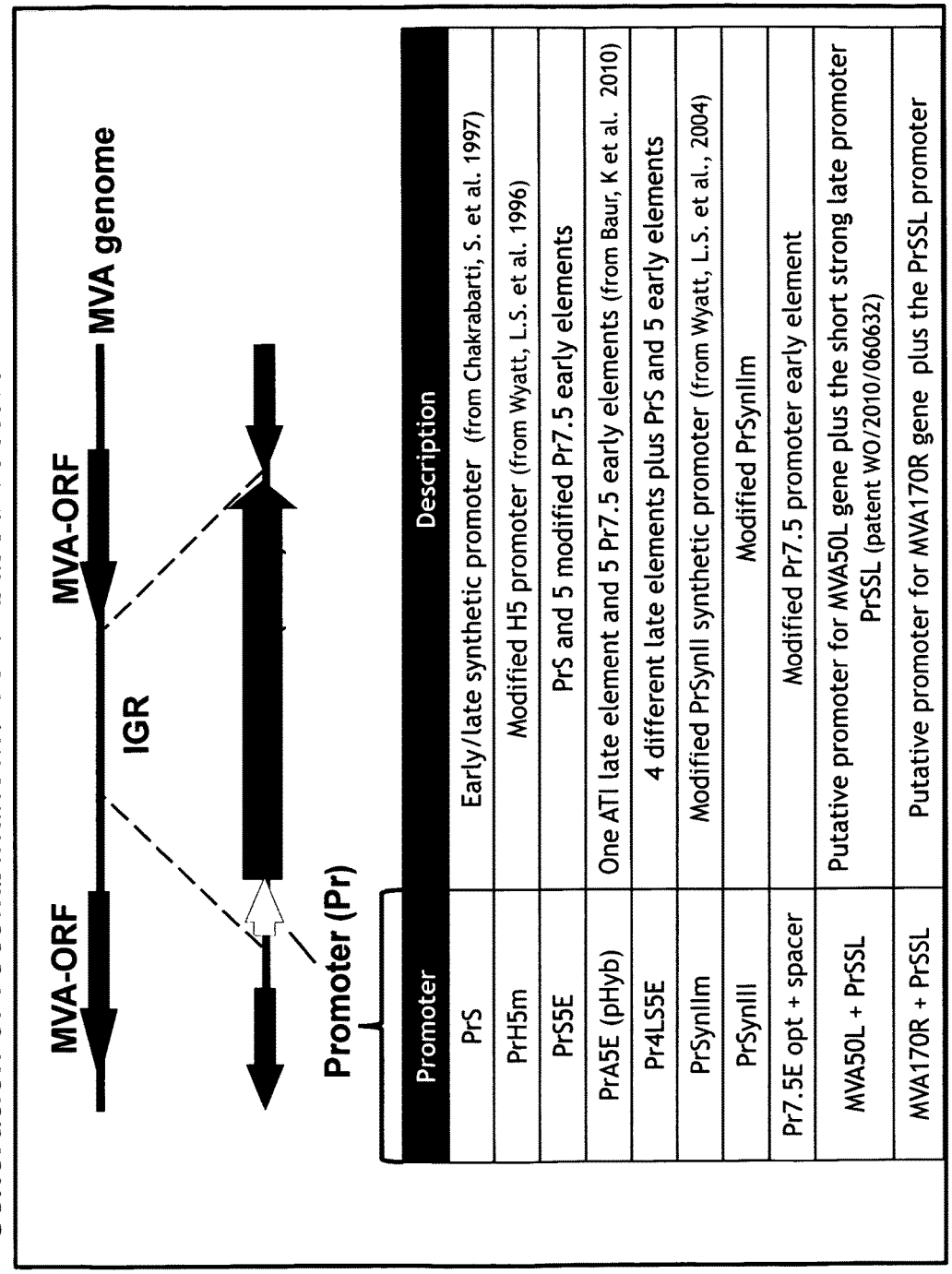
FIG. 1 depicts generation of recombinant MVA-BN constructs. Several recombinant MVA-BN viruses were generated expressing ovalbumin (OVA) as a reporter transgene under the transcriptional control of the different viral promoters listed. The OVA expression cassette was introduced within an intergenic region (IGR) in the MVA genome using recombination techniques. ORF, open reading frame.

It must be noted that, as used herein, the singular forms "a", "an", and "the", include plural references unless the context clearly indicates otherwise. Thus, for example, reference to "an epitope" includes one or more of epitopes and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. When used herein the term "comprising" can be substituted with the term "containing" or "including" or sometimes when used herein with the term "having". Any of the aforementioned terms (comprising, containing, including, having), though less preferred, whenever used herein in the context of an aspect or embodiment of the present invention can be substituted with the term "consisting of".

When used herein "consisting of" excludes any element, step, or ingredient not specified in the claim element. When used herein, "consisting essentially of" does not exclude materials or steps that do not materially affect the basic and novel characteristics of the claim.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

Several documents are cited throughout the text of this specification. Each of the documents cited herein (including all patents, patent applications, scientific publications, manufacturer's specifications, instructions, etc.), whether supra or infra, are hereby incorporated by reference in their entirety. To the extent the material incorporated by reference contradicts or is inconsistent with this specification, the specification will supersede any such material. Nothing herein is to be construed as an admission that the invention is not entitled to antedate such disclosure by virtue of prior invention.

THE INVENTION

The effect of various promoters on the induction of antibody and CTL responses by an MVA encoded antigenic determinant was investigated. A strong early promoter (a combination of 5 early promoter elements in a tandem fashion) was used to enhance expression specifically in the immediate early and early phase of the viral replication cycle. This promoter element, when coupled to a weak late promoter (a short late promoter element derived from the cowpox ATI promoter) has been shown to generate superior acute and memory CD8 T-cell responses compared to Pr7.5- and PrS-driven antigen expression. Baur et al., Journal of Virology, Vol. 84 (17): 8743-8752 (2010).

MVA viral constructs containing the strong early promoter (a combination of 5 early promoter elements in a tandem fashion) fused to a variety of late promoters and various other combinations of early and late promoters were generated and are shown in FIG. 1. The constructs were characterized in vivo by immunization of mice at three timepoints and assessing CTL and antibody responses to the encoded antigen. FIG. 2 shows a schematic of the basic procedure.

Previous reports have shown that early expression of antigens from MVA provides an enhanced CD8 T cell response in mice. Baur et al., 2010. The immediate-early promoter PrA5E (see FIG. 1) showed enhanced T cell responses compared to other known standard promoters, Pr7.5 and PrS, but failed to provide an advantage in terms of antibody responses compared to these same promoters. The PrS and the PrA5E were further compared to other promoters in their ability to elicit cellular and humoral immune responses using OVA as a model antigen.

Mice were immunized at time 0 and at 4 and 8 weeks with recombinant MVA viruses expressing OVA under the control of different promoters, with empty vector, or with PBS. Blood was taken 1 week after each immunization (weeks 1, 5, and 9) for determination of T cell responses.

Strong early mRNA and protein expression kinetics correlated well with strong T cell responses in vivo. As shown in FIGS. 5A. and B. three promoters with strong early transcriptional activity such as the PrA5E, PrS5E and Pr4LS5E induced the strongest T cell responses. Promoters with late kinetics such as the PrSynIIm, PrSynIII, MVA50L+PrSSL and MVA170R+PrSSL were very poor inducers of T cell responses. PrH5m, PrS and Pr7.5 opt+ spacer also induced strong T cell responses.

Blood was also taken three weeks after each immunization (weeks 3, 7, and 11) from the mice immunized at time 0 and at 4 and 8 weeks for determination of antibody responses. MVA and OVA specific antibodies were detected by ELISA. The results are shown in FIGS. 6A. and B.

As shown in FIG. 6A, promoters with late kinetics, such as PrSynIIm, PrSynIII, MVA50L+PrSSL, and MVA170R+ PrSSL showed very low antibody responses after 1 immunization, whereas antibody titers could be detected after the second and third immunization.

Unexpectedly, PrS5E showed a reduced level of antibody production relative to PrA5E after a single immunization (FIG. 6A). Similarly, Pr4LS5E showed a low level of antibody production after a single immunization (FIG. 6B). Also, Pr7.5E opt+spacer showed a low level of antibody production after 1 and 2 immunizations (FIG. 6B). The low antibody production with these promoters was surprisingly even found in the presence of a high CTL response against the antigen.

In summary, the inventors of the present invention surprisingly found that promoters with late kinetics like PrSynIIm, PrSynIII, MVA50L+PrSSL, and MVA170R+ PrSSL as well as with early kinetics such as PrS5E, Pr4LS5E, and Pr7.5E opt+spacer raise a low level of antibody production at least after a first, priming immunization. Such promoters may, thus, be suitable for treating diseases with antibody-dependent enhancement (ADE) like dengue hemorrhagic fever (DHF)—see above.

The invention, thus, encompasses a transcriptional control element comprising a late element driving late expression of an antigenic determinant, wherein said late element is linked to at least two early elements driving early expression of said antigenic determinant, and wherein the late element is stronger than the cowpox ATI promoter in HeLa cells.

Also encompassed by the present invention is a recombinant poxviral vector comprising such a transcriptional control element, as well as a recombinant poxviral vector suitable for inducing an immune response against an antigenic determinant without raising a significant antibody response at least after a first, priming immunization. Such a viral vector comprises a transcriptional control element comprising an early and/or late element linked to a nucleotide sequence encoding the antigenic determinant.

In a particularly preferred embodiment, the recombinant poxviral vector includes the transcriptional control element as described above, i.e., a transcriptional control element comprising a late element linked to at least two early elements, wherein the late element is stronger than the cowpox ATI promoter in HeLa cells.

The invention additionally encompasses a recombinant poxviral vector comprising the early element of the Pr7.5 promoter (Pr7.5E), wherein said early element is optimized (Pr7.5E opt) and fused to a 3' spacer of at least 3 to 6 bp (Pr7.5E opt+spacer) linked to a nucleotide sequence encoding an antigenic determinant. Such a vector is also in particular suitable for inducing an immune response against the antigenic determinant without raising a significant antibody response after a first, priming immunization.

Likewise, the present invention is also related to the use of the recombinant viral vectors for the preparation of a corresponding medical compound, to a corresponding method of inducing such an immune response and to pharmaceutical compositions.

Recombinant Poxviruses

Preferably, the poxvirus vector is derived from poxviruses belonging to the Chordopoxvirinae subfamily. Poxviruses include those belonging to the genera Orthopoxvirus, Parapoxvirus, Avipoxvirus, Capripoxvirus, Lepripoxvirus, Suipoxvirus, Molluscipoxvirus and Yatapoxvirus. Most preferred are poxviruses belonging to the genera Orthopoxvirus and Avipoxvirus.

Other poxviruses such as racoonpox and mousepox may be employed in the present invention, for example, for the manufacture of wild-life vaccine. Members of the capripoxvirus and leporipox are also included herein as they may be useful as vectors for cattle and rabbits, respectively.

In other embodiments, the poxvirus is derived from avipoxviruses. Examples of avipoxviruses suitable for use in the present invention include any avipoxvirus such as fowlpoxvirus, canarypoxvirus, uncopoxvirus, mynahpoxvirus, pigeonpoxvirus, psittacinepoxvirus, quailpoxvirus, peacockpoxvirus, penguinpoxvirus, sparrowpoxvirus, starlingpoxvirus and turkeypoxvirus. Preferred avipoxviruses are canarypoxvirus and fowlpoxvirus.

Avipoxviruses are naturally host-restricted and productively replicate only in avian species and cells (Taylor et al., Biological and immunogenic properties of a canarypox-rabies recombinant, ALVAC-RG (vCP65) in non-avian species, Vaccine 13:539-549, 1995). If human cells are infected with an avipoxvirus, heterologous genes are expressed from the viral genome. However, the avipoxvirus does not replicate in the human cells and there is, thus, no risk that the human being is harmed by productive virus replication. Various recombinant avipoxviruses have been constructed that express e.g. lentiviral gene products (U.S. Pat. No. 5,766,598), cytokines and/or tumor-associated antigens (U.S. Pat. No. 5,833,975) or rabies G glycoprotein (Taylor et al., Biological and immunogenic properties of a canarypox-rabies recombinant, ALVAC-RG (vCP65) in non-avian species, Vaccine 13: 539-549, 1995). A recombinant canarypox virus expressing the four HIV genes gag, pol, env and nef has already been used in clinical trials (Peters, B. S., The basis for HIV immunotherapeutic vaccines, Vaccine 20: 688-705, 2001).

Since avipoxviruses productively replicate only in avian cells, these cells have to be used for the amplification of the virus and for the generation of recombinant viruses.

An example for a canarypox virus is strain Rentschler. A plaque purified Canarypox strain termed ALVAC (U.S. Pat. No. 5,766,598) was deposited under the terms of the Budapest treaty with the American Type Culture Collection (ATCC), accession number VR-2547. Another Canarypox strain is the commercial canarypox vaccine strain designated LF2 CEP 524 24 10 75, available from Institute Merieux, Inc.

Examples of a Fowlpox virus are strains FP-1, FP-5 and TROVAC (U.S. Pat. No. 5,766,598). FP-1 is a Duvette strain modified to be used as a vaccine in oneday old chickens. The strain is a commercial fowlpox virus vaccine strain designated 0 DCEP 25/CEP67/239 October 1980 and is available from Institute Merieux, Inc. FP-5 is a commercial fowlpox virus vaccine strain of chicken embryo origin available from American Scientific Laboratories (Division of Schering Corp.) Madison, Wis., United States Veterinary License No. 165, serial No. 30321.

In a particularly preferred embodiment of the invention, the replication deficient recombinant virus is an orthopoxvirus, such as a vaccinia virus. Most preferred is modified vaccinia virus Ankara (MVA), which will be described in further detail below.

Examples for vaccinia viruses suitable for use in the present invention include the vaccinia virus strain DIs, which grows well in CEF cells but is unable to grow in most mammalian cells (Tagaya et al., A new mutant of dermovaccinia virus, Nature Vol. 192, No. 4800, 381-383, 1961; Ishii et al., Structural analysis of vaccinia virus DIs strain: Application as a new replication-deficient viral vector, Virology 302, 433-444, 2002).

Another preferred example of a suitable vaccinia virus is the highly attenuated vaccinia virus strain NYVAC, which was derived from a plaque-cloned isolate of the Copenhagen vaccine strain by deletion of 18 ORFs from the viral genome (Tartaglia et al., NYVAC: A highly attenuated strain of vaccinia virus, Virology 188, 217-232, 1992). NYVAC is characterized by a dramatically reduced ability to replicate on a variety of human tissue culture cells, but retains the ability to induce strong immune responses to extrinsic antigens.

All of the above-described viruses are equally suitable for use in the present invention.

Modified Vaccinia Ankara Viruses

Modified vaccinia virus Ankara (MVA) is related to Vaccinia virus, a member of the genus Orthopoxvirus in the family Poxviridae. MVA originates from the dermal vaccinia strain Ankara (Chorioallantois vaccinia Ankara (CVA) virus) that was maintained in the Vaccination Institute, Ankara, Turkey for many years and used as the basis for vaccination of humans. However, due to the often severe post-vaccinal complications associated with vaccinia viruses (VACV), there were several attempts to generate a more attenuated, safer smallpox vaccine.

MVA has been generated by 516 serial passages on chicken embryo fibroblasts of the CVA virus (for review see Mayr, A., et al., Passage History: Abstammung, Eigenschaften and Verwendung des attenuierten Vaccinia-Stammes MVA, Infection 3, 6-14, 1975). As a consequence of these long-term passages the resulting MVA virus deleted about 31 kilobases of its genomic sequence and, therefore, was described as highly host cell restricted to avian cells (Meyer, H. et al., Mapping of deletions in the genome of the highly attenuated vaccinia virus MVA and their influence on virulence, J. Gen. Virol. 72, 1031-1038, 1991; Meisinger-Henschel et al., Genomic sequence of chorioallantois vaccinia virus Ankara, the ancestor of modified vaccinia virus Ankara, J. Gen. Virol. 88, 3249-3259, 2007.) It was shown, in a variety of animal models that the resulting MVA was significantly avirulent (Mayr, A. & Danner, K. Vaccination against pox diseases under immunosuppressive conditions, Dev. Biol. Stand. 41: 225-34, 1978).

Additionally, MVA has been tested in clinical trials as vaccine to immunize against the human smallpox disease (Mayr et al., Zbl. Bakt. Hyg. I, Abt. Org. B 167, 375-390 [1987], Stickl et al., MVA vaccination against smallpox: clinical tests with an attenuated live vaccinia virus strain (MVA) (author's transl), Dtsch. med. Wschr. 99, 2386-2392, 1974). As part of the early development of MVA as a pre-smallpox vaccine, there were clinical trials using MVA-517 (corresponding to the 517th passage) in combination with Lister Elstree (Stickl, 1974, Smallpox vaccination and its consequences: first experiences with the highly attenuated smallpox vaccine "MVA". Prev. Med. 3(1): 97-101; Stickl and Hochstein-Mintzel, 1971, Intracutaneous smallpox vaccination with a weak pathogenic vaccinia virus ("MVA virus"). Munch Med Wochenschr. 113: 1149-1153) in subjects at risk for adverse reactions from vaccinia. In 1976, MVA derived from MVA-571 seed stock (corresponding to the 571st passage) was registered in Germany as the primer vaccine in a two-stage parenteral smallpox vaccination program. Subsequently, MVA-572 was used in approximately 120,000 Caucasian individuals, the majority children between 1 and 3 years of age, with no reported severe side effects, even though many of the subjects were among the population with high risk of complications associated with conventional vaccinia virus (Mayr et al., 1978, The smallpox vaccination strain MVA: marker, genetic structure, experience gained with the parenteral vaccination and behaviour in organisms with a debilitated defence mechanism (author's transl). Zentralbl. Bacteriol. (B) 167: 375-390). MVA-572 was deposited at the European Collection of Animal Cell Cultures, Vaccine Research and Production Laboratory, Public Health Laboratory Service, Centre for Applied Microbiology and Research, Porton Down, Salisbury, Wiltshire SP4 OJG, United Kingdom, as ECACC V94012707.

Being that many passages were used to attenuate MVA, there are a number of different strains or isolates, depending on the passage number in CEF cells. All MVA strains originate from Dr. Mayr and most are derived from MVA-572 that was used in Germany during the smallpox eradication program, or MVA-575 that was extensively used as a veterinary vaccine. MVA-575 was deposited on Dec. 7, 2000, at the European Collection of Animal Cell Cultures (ECACC) with the deposition number V00120707.

The invention encompasses recombinant MVA viruses generated with any and all MVA viruses. Besides MVA-572 and -575, a further example for an MVA strain is deposit VR-1508, deposited at the American Type Culture collection (ATCC), Manassas, Va. 20108, USA. Derivatives/variants of these strains are also preferred.

By serial propagation (more than 570 passages) of the CVA on primary chicken embryo fibroblasts, the attenuated CVA-virus MVA (modified vaccinia virus Ankara) was obtained. MVA was further passaged by Bavarian Nordic and is designated MVA-BN. Both, MVA as well as MVA-BN lacks approximately 13% (26.5 kb from six major and multiple minor deletion sites) of the genome compared with ancestral CVA virus. The deletions affect a number of virulence and host range genes, as well as a large fragment of the gene coding for A-type inclusion protein (ATI) and a gene coding for a structural protein directing mature virus particles into A-type inclusion bodies. A sample of MVA-BN was deposited on Aug. 30, 2000, at the European Collection of Cell Cultures (ECACC) under number V00083008.

Particularly preferred MVA viruses are, thus, MVA-BN as, e.g., deposited at ECACC under number V00083008 and MVA variant strains having the same properties as MVA-BN.

MVA-BN can attach to and enter human cells where virally-encoded genes are expressed very efficiently. However, assembly and release of progeny virus does not occur. Preparations of MVA-BN and derivatives have been administered to many types of animals, and to more than 2000 human subjects, including immunodeficient individuals. All vaccinations have proven to be generally safe and well tolerated. The perception from many different publications is that all MVA strains are the same and represent a highly attenuated, safe, live viral vector. However, preclinical tests have revealed that MVA-BN demonstrates superior attenuation and efficacy compared to other MVA strains (WO 02/42480).

In a preferred embodiment, the MVA according to the invention has the capability of reproductive replication in vitro in chicken embryo fibroblasts (CEF), but no capability of reproductive replication in human cells in which MVA 575 or MVA 572 can reproductively replicate. Most preferably, the MVA has no capability of reproductive replication in the human keratinocyte cell line HaCaT, the human embryo kidney cell line 293, the human bone osteosarcoma cell line 143B, and the human cervix adenocarcinoma cell line HeLa. In preferred embodiments, the MVA virus is characterized by having the capability of reproductive replication in vitro in chicken embryo fibroblasts (CEF) and by being more attenuated than MVA-575 in the human keratinocyte cell line HaCaT, in the human bone osteosarcoma cell line 143B, and in the human cervix adenocarcinoma cell line HeLa. Preferably, the MVA virus is capable of a replication amplification ratio of greater than 500 in CEF cells.

Further, MVA-BN strains fail to replicate in a mouse model that is incapable of producing mature B and T cells, and as such is severely immune compromised and highly susceptible to a replicating virus. An additional or alternative property of MVA-BN strains is the ability to induce at least substantially the same level of immunity in vaccinia virus prime/vaccinia virus boost regimes when compared to DNA-prime/vaccinia virus boost regimes.

The term "not capable of reproductive replication" is used in the present application as defined in WO 02/42480 and U.S. Pat. No. 6,761,893, respectively. Thus, said term applies to a virus that has a virus amplification ratio at 4 days after infection of less than 1 using the assays described in U.S. Pat. No. 6,761,893, which assays are hereby incorporated by reference. The "amplification ratio" of a virus is the ratio of virus produced from an infected cell (Output) to the amount originally used to infect the cells in the first place (Input). A ratio of "1" between Output and Input defines an amplification status wherein the amount of virus produced from the infected cells is the same as the amount initially used to infect the cells.

In a most preferred embodiment, the MVA strain used in the present invention is MVA-BN or a derivative thereof. The features of MVA-BN, the description of biological assays allowing evaluating whether an MVA strain is MVA-BN or a derivative thereof and methods allowing to obtain MVA-BN or an MVA having the properties of MVA-BN are disclosed in WO 02/42480. The content of this application is included in the present application by reference.

In particular, reference is made to the definition of the properties of the MVA according to the invention as described in WO 02/42480, such as the properties of MVA-BN and the properties and definitions of the derivates of MVA-BN. Said reference also discloses how MVA and other vaccinia viruses can be propagated. Briefly, eukaryotic cells are infected with the virus. The eukaryotic cells are cells that are susceptible to infection with the respective poxvirus and allow replication and production of infectious virus. For MVA an example for this type of cells are chicken embryo fibroblasts (CEF) and BHK cells (Drexler et al., Highly attenuated modified vaccinia Ankara replicates in baby hamster kidney cells, a potential host for virus propagation, but not in various human transformed and primary cells, J. Gen. Virol. 79, 347-352, 1998). CEF cells can be cultivated under conditions known to the person skilled in the art. Preferably the CEF cells are cultivated in serum-free medium in stationary flasks or roller bottles. The incubation preferably takes place 48 to 96 hours at 37° C. For the infection MVA is preferably used at a multiplicity of infection (MOI) of 0.05 to 1 $TCID_{50}$ and the incubation preferably takes place 48 to 72 hours at 37° C.

WO 02/42480 discloses how vaccinia viruses are obtained having the properties of MVA-BN. The highly attenuated MVA-BN virus can be derived, e.g., by the further passage of a modified vaccinia virus Ankara (MVA), such as MVA-572 or MVA-575.

MVA-BN or its derivatives are, according to one embodiment, characterized by inducing at least substantially the same level of immunity in vaccinia virus prime/vaccinia virus boost regimes when compared to DNA-prime/vaccinia virus boost regimes. A vaccinia virus is regarded as inducing at least substantially the same level of immunity in vaccinia virus prime/vaccinia virus boost regimes when compared to DNA-prime/vaccinia virus boost regimes if the CTL response as measured in one of the "assay 1" and "assay 2" as disclosed in WO 02/42480, preferably in both assays, is at least substantially the same in vaccinia virus prime/vaccinia virus boost regimes when compared to DNA-prime/vaccinia virus boost regimes. More preferably, the CTL response after vaccinia virus prime/vaccinia virus boost administration is higher in at least one of the assays, when compared to DNA-prime/vaccinia virus boost regimes. Most preferably, the CTL response is higher in both assays.

In summary, MVA-BN has been shown to have the highest attenuation profile compared to other MVA strains and is safe even in severely immunocompromised animals.

Although MVA exhibits strongly attenuated replication in mammalian cells, its genes are efficiently transcribed, with the block in viral replication being at the level of virus assembly and egress. (Sutter and Moss, 1992, Nonreplicating vaccinia vector efficiently expresses recombinant genes. Proc. Natl. Acad. Sci. U.S.A 89: 10847-10851; Carroll and Moss, 1997, Host range and cytopathogenicity of the highly attenuated MVA strain of vaccinia virus: propagation and generation of recombinant viruses in a nonhuman mammalian cell line. Virology 238: 198-211.) Despite its high attenuation and reduced virulence, in preclinical studies MVA-BN has been shown to elicit both humoral and cellular immune responses to VACV and to the products of heterologous genes cloned into the MVA genome (Harrer et al., Therapeutic Vaccination of HIV-1-infected patients on HAART with recombinant HIV-1 nef-expressing MVA: safety, immunogenicity and influence on viral load during treatment interruption. Antiviral Therapy 10: 285-300, 2005; Cosma et al., Therapeutic vaccination with MVA-HIV-1 nef elicits Nef-specific T-helper cell responses in chronically HIV-1 infected individuals, Vaccine 22(1): 21-29, 2003; Di Nicola et al., Clinical protocol. Immunization of patients with malignant melanoma with autologous CD34(+) cell-derived dendritic cells transduced ex vivo with a recombinant replication-deficient vaccinia vector encoding the human tyrosinase gene: a phase I trial. Hum Gene Ther. 14(14): 1347-1360, 2003; Di Nicola et al., Boosting T cell-mediated immunity to tyrosinase by vaccinia virus-transduced, CD34(+)-derived dendritic cell vaccination: a phase I trial in metastatic melanoma. Clin Cancer Res. 10(16): 5381-5390, 2004)

MVA-BN and recombinant MVA-BN-based vaccines can be generated, passaged, produced and manufactured in CEF cells cultured in serum-free medium. Many recombinant MVA-BN variants have been characterized for preclinical and clinical development. No differences in terms of the attenuation (lack of replication in human cell lines) or safety (preclinical toxicity or clinical studies) have been observed between MVA-BN, the viral vector backbone, and the various recombinant MVA-based vaccines.

Transcriptional Control Elements

As used herein, transcriptional control elements or sequences are DNA regulatory sequences, such as promoter sequences to bind RNA polymerase, enhancers, translation initiation sequences for ribosome binding and/or terminators, and the like, that provide for the expression of an antigen of interest in a host cell.

Transcriptional control elements can be derived from promoters. In a preferred embodiment, the transcriptional control element is a promoter and/or promoter element, preferably a poxviral promoter and/or promoter element. The promoter is, preferably, an early/late promoter, in particular an early/late hybrid promoter comprising a late element derived from a promoter different to the one from which the early element is derived. An early/late promoter drives expression of a linked nucleic acid sequence at both early and late times of the viral lifecycle.

As used herein, the term "early promoter" or "early promoter element" refers to promoters that are active in virus infected cells, before viral DNA replication has occurred.

Methods are known to the person skilled in the art how it can be determined whether a promoter is an early promoter. In particular, the promoter of interest can be inserted upstream of a reporter gene and said construct can be introduced into a viral vector, e.g. a vaccinia virus vector which is then used to infect cells. In order to assess for the activity as early promoter the cells are incubated with a substance that inhibits viral DNA replication such as AraC. DNA replication is a prerequisite for the late promoter activity. Thus, any promoter activity that is measured in this assay system is due to elements active as early promoter. Consequently, the term "late promoter" refers to any promoters that are active after DNA replication has taken place. The late activity can also be measured by methods known to the person skilled in the art. For the sake of simplicity the term "late promoter" as used in the present application refers to a promoter that is only active if no substance is added that blocks DNA replication.

Early and late expression from hybrid early/late promoters can be determined by infecting host cells like CEF and Hela cells, for example. The levels can be compared to the expression levels of a construct containing the PrS promoter (SEQ ID NO:10) in the presence and absence of AraC, for example, at 40 µg/ml. See Chakrabarti et al., Compact, Synthetic, Vaccinia Virus Early Late Promoter for Protein Expression. BioTechneques 23: 1094-1097, 1997.

In further preferred embodiments the late element is derived from the PrS, PrSSL, Pr123L, and/or Pr124L promoter, whereas the early element is, preferably, the Pr7.5 early promoter element, in particular an optimized p7.5 early promoter element.

The transcriptional control element comprises at least 2, preferably at least 5 copies of the early element, preferably at least two, three, four, five, six, seven, eight, nine, ten, or more copies of an early promoter, preferably an immediate early promoter element, more preferably a p7.5 early promoter element.

Within the context of this invention, an "optimized Pr7.5 promoter" or "optimized Pr7.5E promoter/element" means a Pr7.5 promoter/element modified at 4 nucleotide positions within the A-rich critical core region of 16 nucleotides as described in Davison, A. J. and B. Moss. 1989. Structure of vaccinia virus early promoters. J. Mol. Biol. 210:749-769. The sequence of said optimized Pr7.5E promoter element are nucleotides (nt) 1-16 of SEQ ID NO:4.

To said optimized promoter element further nucleotides, in particular nt 17-34 of SEQ ID NO:4, were added. Thus, the early element of the transcriptional control element according to the present invention preferably comprises nt 1-34, in particular nt 17-34 of SEQ ID NO:4 or the sequence of SEQ ID NO:12.

In some embodiments, the promoter comprises or consists of a single copy of an optimized Pr7.5E promoter. In some embodiments, the vector comprises a single copy of an optimized Pr7.5E promoter.

In further embodiments, the promoter and, thus, also the vectors including the promoter, comprises or consists of a single copy of an optimized Pr7.5E promoter fused to a 3' spacer of at least 3-6 bp or at least 7-18 bp. The spacer may be 10, 15, 20, 25, 30, 35, 40, 45, 50 or even more bp. Preferably, the spacer is 7, 8, 9, 10, 11, 12, 13, 14, 15, 16, 17, or 18 bp. Most preferably, the spacer is 12 bp and comprises, in particular, nt 35-46 of SEQ ID NO:4.

Most preferred is a transcriptional control element or promoter comprising the nucleotide sequence of SEQ ID NO:4. In some embodiments, the promoter comprises or consists of the sequence of SEQ ID NO:12 or SEQ ID NO:4. In some embodiments, the vector comprises one or more copies of the nucleotide sequence of SEQ ID NO:12 or SEQ ID NO:4.

According to the present invention, the recombinant poxvirus includes a late element of the transcriptional control element which is preferably stronger than the cowpox ATI promoter in HeLa cells.

Whether a late promoter is "stronger than the cowpox ATI promoter in HeLa cells" can be determined by linking the promoter to a marker gene within an MVA construct. This construct can then be compared to the same construct containing the ATI cowpox promoter (SEQ ID NO:11) by infecting HeLa cells with each of the constructs and measuring marker gene mRNA production in the presence and absence of AraC at 4 hours after infection (See Baur et al., 2010, which is hereby incorporated by reference). The difference in mRNA expression between +Ara C and −AraC is the mRNA signal due to late promoter expression. Within the context of this invention, a promoter is "stronger than the cowpox ATI promoter in HeLa cells" if the level of RNA from the promoter is at least 1.5-fold greater than that produced by the cowpox ATI promoter (SEQ ID NO:11) in the assay described above.

Within the context of this invention, the PrS and Pr4L promoter or promoter element are late promoters or promoter elements that are stronger than the cowpox ATI promoter in HeLa cells.

In some embodiments, the level of RNA from the promoter is at least 2-fold, at least 3-fold, at least 4-fold, at least 5-fold, at least 10-fold, or at least 20-fold greater than that produced by the cowpox ATI promoter in the assay described above.

Preferably, the early/late hybrid promoter comprises at least one late promoter stronger than the cowpox ATI promoter, linked to at least two, three, four, five, six, seven, eight, nine, ten, or more copies of an early promoter, preferably an immediate early promoter element, more preferably a Pr7.5E early promoter element.

In some embodiments, the late promoter comprises a PrS promoter, a PrSSL promoter, a Pr123L promoter, or a Pr124L promoter.

Some embodiments encompass the early/late hybrid promoter comprising at least 5 copies of an optimized Pr7.5E early promoter element.

Preferably, the transcriptional control element comprises the nucleotide sequence of SEQ ID NO:2, SEQ ID NO:3, SEQ ID NO:4, SEQ ID NO:5, SEQ ID NO:6, SEQ ID NO:7 or SEQ ID NO:13. Most preferred are transcriptional control elements comprising the nucleotide sequence of SEQ ID NO:2, SEQ ID NO:3 or SEQ ID NO:4.

In some embodiments, the transcriptional control element comprises a sequence that is at least 50%, 55%, 60%, 65%, 70%, 75%, 80%, 85%, 90%, 95%, 98%, or 99% identical to the nucleotide sequence of SEQ ID NO:2, SEQ ID NO:3, SEQ ID NO:4, SEQ ID NO:5, SEQ ID NO:6, SEQ ID NO:7 or SEQ ID NO:13 and has approximately the same early and/or late activity as the promoters or elements of SEQ ID NO:2, SEQ ID NO:3, SEQ ID NO:4, SEQ ID NO:5, SEQ ID NO:6, SEQ ID NO:, or SEQ ID NO:13. Most preferred is an at least 70% identity to said sequences.

The percent identity may be determined by visual inspection and mathematical calculation. Alternatively, the percent identity of two nucleic acid sequences can be determined by comparing sequence information using the GAP computer program, version 6.0 described by Devereux et al. (Nucl. Acids Res. 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps. Other programs used by one skilled in the art of sequence comparison may also be used.

Based on knowledge of the consensus sequences of early and late promoters, as well as knowledge regarding the effects of various nucleotide substitutions on early and late promoter activity (Davison and Moss, J. Mol. Biol. 210: 771-784, 1989; Davison and Moss, J. Mol. Biol. 210:749-769, 1989), many changes to the promoter of SEQ ID NO:2, SEQ ID NO:3, SEQ ID NO:4, SEQ ID NO:5, SEQ ID NO:6, SEQ ID NO:7, or SEQ ID NO:13 can be envisioned that would not negatively affect the activity of the promoter. Nucleotide sequences that differ from SEQ ID NO:2, SEQ ID NO:3, SEQ ID NO:4, SEQ ID NO:5, SEQ ID NO:6, SEQ ID NO:7, or SEQ ID NO:13 in one or more positions, but have approximately the same (i.e., +/−20%) early and late promoter activity as that of the promoter of SEQ ID NO:2, SEQ ID NO:3, SEQ ID NO:4, SEQ ID NO:5, SEQ ID NO:6, SEQ ID NO:7, and SEQ ID NO:13, respectively, are encompassed by this invention.

Further encompassed by the present invention is a nucleotide sequence comprising the sequence of SEQ ID NO:2, SEQ ID NO:3, SEQ ID NO:4, SEQ ID NO:5, SEQ ID NO:6, SEQ ID NO:7 and/or SEQ ID NO:13, preferably of SEQ ID NO:2, SEQ ID NO:3 and/or SEQ ID NO:4, and/or comprising a sequence having at least 70% identity to SEQ ID NO:2, SEQ ID NO:3, SEQ ID NO:4, SEQ ID NO:5, SEQ ID NO:6, SEQ ID NO:7, and/or SEQ ID NO:13, preferably to SEQ ID NO:2, SEQ ID NO:3 and/or SEQ ID NO:4.

Also encompassed is a nucleotide sequence comprising nt 1-34, in particular nt 17-34, and/or nt 35-46 of SEQ ID NO:4 and/or a sequence having at least 70% identity to nt 1-34, in particular nt 17-34, and/or nt 35-46 of SEQ ID NO:4.

Antigenic Determinants

The present invention is, inter alia, directed to recombinant viruses comprising an antigenic determinant.

The term "recombinant virus" refers to any virus that comprises an additional heterologous nucleic acid that is not naturally part of the viral genome. A heterologous or recombinant gene can be, e.g. a gene encoding a viral, bacterial, fungal or cancer/tumor antigen, a therapeutic gene, a gene coding for a peptide comprising at least one epitope to induce an immune response. Further examples for heterologous genes comprise an antisense expression cassette or a ribozyme gene. In preferred embodiments, the encoded antigenic determinant is a bacterial, viral, or tumour antigen. Preferably, the antigenic determinant is a foreign antigenic determinant to the host.

The term "antigenic determinant" encompasses "antigens" as well as "epitopes" or "antigenic epitopes". "Antigen" refers to a molecule which contains one or more epitopes that stimulate a host's immune system to make a cellular antigen-specific immune response, or a humoral antibody response. Antigens may include proteins, polypeptides, antigenic protein fragments and the like. Furthermore, the antigen can be derived from any known virus, bacterium, parasite, prion, plants, protozoans, or fungus and can be a whole organism. The term also includes tumor antigens and antigenic determinants, respectively. Synthetic antigens such as polyepitopes, flanking epitopes, and other recombinant or synthetically derived antigens are also included in this application. In a preferred embodiment, the antigen in the present invention is a polypeptide or protein.

As used herein, the terms "antigenic determinant, "antigen" or "antigenic epitope" are used synonymously to refer to a short peptide sequence or oligosaccharide which is specifically recognized or specifically bound by a component of the immune system. Generally, antigenic determinants are recognized in the context of an MHC/HLA molecule to which they are bound on an antigen presenting cell.

In relation to the term "epitope", the term "antigen" refers to a (longer) sequence, in particular a (longer) amino acid sequence or protein sequence, whereas the phrase "antigenic epitope" or "an epitope of the antigen" encompasses a stretch of shorter sequence from the longer sequence. The term "antigen" thus encompasses epitopes. The term "antigen" also includes variants of proteins, polypeptides, and antigenic protein fragments as described herein. Also, the term "antigen" encompasses sequences identical to the native sequence as well as modification to the native sequence, such as deletions, additions, insertions and substitutions.

An epitope, also termed herein as "antigenic epitope", forms part of the antigen that still elicit an immune response in a host. An epitope is, however, not limited to the exact sequence of the antigen from which it is derived. Thus, the term "epitope" encompasses sequences identical to the native sequence as well as modification to the native sequence, such as deletions, additions, insertions and substitutions. Preferably, an epitope variant have at least about 50%, at least about 60% or 65%, at least about 70% or 75%, at least about 80%, 81%, 82%, 83%, 84%, 85%, 86%, 87%, 88%, or 89%, more typically, at least about 90%, 91%, 92%, 93%, or 94% and even more typically at least about 95%, 96%, 97%, 98% or 99%, most typically, at least about 99% amino acid identity with the reference epitope (i.e. the epitope from which it is derived).

Any antigenic determinant can be expressed by the recombinant viruses of the invention. Viral, bacterial, fungal, and cancer or tumor antigens are preferred. Particularly preferred examples of virus antigens suitable for use in the present invention comprise antigens from Retroviruses (including HIV-1 and HTLV), Herpesviruses (including Cytomegalovirus), Flaviviruses (including Denguevirus), Orthomyxoviruses, Paramyxoviruses (including Measles virus, Mumps virus, Respiratory syncytial virus), Togaviruses (including *Rubella* virus), Hepatitis viruses, Hepadnaviruses, Influenza virus, Picornaviruses (including such as Poliovirus), Coronaviruses, Bunyaviruses, Arenaviruses, Filoviruses or from other viruses causing hemorrhagic fever. Preferred are antigens from Flaviviruses, in particular from Denguevirus.

Examples of preferred cancer antigens include prostate-specific antigen (PSA), prostatic acid phosphatase (PAP) antigen and Her-2/neu antigens.

Preferred bacterial antigens include anthrax antigens.

Kits Comprising Recombinant Viruses

The invention provides kits comprising a recombinant virus of the invention, preferably a recombinant MVA according to the present invention. The kit can comprise at least one, two, three, four, or more containers or vials of the recombinant virus, together with instructions for the administration of the virus to a subject. In a preferred embodiment, the subject is a human. The instructions can indicate that the recombinant virus is administered to the subject in multiple (i.e., 2, 3, 4, 5, 6, etc.) dosages at specific timepoints (e.g., at least 4 weeks, at least 6 weeks, at least 8 weeks after the previous administration). Preferably, the instructions indicate that the recombinant virus is to be administered in at least 3 or at least 4 dosages.

Preferably, a kit for vaccination comprises a virus vector according to the present invention for the first vaccination ("priming") in a first vial/container and for an at least second, third and/or further vaccination ("boosting") in a second/third/further vial/container.

Methods of Affecting an Immune Response

The invention encompasses methods of affecting an immune response against an antigenic determinant in a host, including a human, without raising a significant antibody response after a first, priming immunization. In a preferred embodiment, said immune response is a T cell response, in particular a strong T cell response, preferably a CD8 T cell response.

As used herein, the term "affecting a T cell response" is to be understood that a T cell response is induced, raised and/or enhanced by the methods of the present invention.

Within the context of this invention, a "strong" T cell response, in particular CD8 T cell response, against an antigenic determinant in a host means a T cell response that demonstrates at least 50% of neoantigen-specific T cells generated with the same MVA construct containing the PrS promoter (SEQ ID NO:10) after a single immunization. Preferably, the T cell response demonstrates a higher percentage of neoantigen-specific T cells than the percentage generated with the same MVA construct containing the PrS promoter (SEQ ID NO:10) after a single immunization. In some embodiments, the T cell response demonstrates at least a 1.5-fold or 2-fold higher percentage of neoantigen-specific T cells than the percentage generated with the same MVA construct containing the PrS promoter (SEQ ID NO:10) after a single immunization.

Within the context of this invention, a "strong antibody response" means an antibody titer that is at least two-fold greater than the antibody titer obtained with the same MVA construct containing the PrS promoter (SEQ ID NO:10) after a single immunization. Thus, within the context of this invention, the "absence of a strong antibody response" means less than the antibody titer obtained with the same MVA construct containing the PrS promoter (SEQ ID NO:10) after a single immunization. Preferably, the antibody titer is half of the titer obtained with the same MVA construct containing the PrS promoter (SEQ ID NO:10) after a single immunization. In some embodiments, the antibody titer is at least 2-fold, at least 4-fold, at least 6-fold, at least 8-fold or at least 10-fold less than the antibody titer obtained with the same MVA construct containing the PrS promoter (SEQ ID NO:10) after a single immunization.

Whether a recombinant MVA induces a "strong immune response against an antigenic determinant" can be determined as described in the examples herein. For example, Pr7.5E opt+spacer, Pr4LS5E, prH5m, PrS5E, and PrA5E all induce a "strong T cell response", in particular a "strong CD8 T cell response" as herein defined. Pr7.5 opt+spacer, Pr4LS5E, PrS5E, PrSynIIm, PrSynIII, MVA50L+PrSSL and MVA170R+PrSSL all do not induce a "strong antibody response" after a first, priming immunization, whereas PrH5m and PrA5E induce a "strong antibody response," as herein defined.

Administration to a Host

The recombinant virus according to the invention can be used for the treatment of a wide range of mammals including humans and even immune-compromised humans. Hence, the present invention also provides a pharmaceutical composition and a vaccine comprising the recombinant virus of the present invention for inducing an immune response in a living animal body, including a human. Furthermore, the present invention also comprises the recombinant virus for use as a pharmaceutical substance.

In the context of the present invention the term "animal body" covers also human beings. More generally, the animal is a vertebrate animal, preferably a mammalian animal including a human. Specific examples for animals are pets such as dogs, cats, economically important animals such as calves, cattle, sheep, goats, horses, pigs and other animal such as mice, rats. The invention may also be used for economically important birds such as turkeys, ducks, goose and hens if viruses are used that are capable to infect the bird's cells but not capable of being replicated to infectious progeny virus in said cells.

The vaccine preferably comprises the recombinant poxviral vector in a concentration range of $10^2$ to 109 or $10^4$ to $10^9$ TCID (tissue culture infectious dose)$_{50}$/ml, preferably in a concentration range of $10^6$ to $5 \times 10^8$ TCID$_{50}$/ml, more preferably in a concentration range of $10^6$ to $10^8$ TCID$_{50}$/ml, and most preferably in a concentration range of $10^7$ to $10^8$ TCID$_{50}$/ml, or at least $2\text{-}5 \times 10^7$ to $10^8$ or $2\text{-}5 \times 10^8$ to $10^9$, especially $10^8$ TCID$_{50}$/ml.

A preferred vaccination dose for humans comprises $10^6$ to $10^9$ TCID$_{50}$, most preferably a dose of $10^7$ TCID$_{50}$ or $10^8$ TCID$_{50}$, especially $10^8$ TCID$_{50}$.

The pharmaceutical composition may generally include one or more pharmaceutically acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycollic acids, polymeric amino acids, amino acid copolymers, lipid aggregates, or the like.

For the preparation of vaccines, the recombinant poxvirus according to the invention can be converted into a physiologically acceptable form. This can be done based on the experience in the preparation of poxvirus vaccines used for vaccination against smallpox (as, for example, described by Stickl et al. 1974).

For example, the purified virus can be stored at $-80°$ C. with a titre of $5 \times 10^8$ TCID$_{50}$/ml formulated in about 10 mM Tris, 140 mM NaCl pH 7.4. For the preparation of vaccine shots, e.g., $10^2\text{-}10^8$ particles of the virus can be lyophilized in 100 ml of phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other aids such as antioxidants or inert gas, stabilizers or recombinant proteins (e.g. human serum albumin) suitable for in vivo administration. The glass ampoule is then sealed and can be stored between 4° C. and room temperature for several months. However, as long as no need exists the ampoule is stored preferably at temperatures below −20° C.

For vaccination or therapy, the lyophilisate can be dissolved in an aqueous solution, preferably physiological saline or Tris buffer, and administered either systemically or locally, i.e. parenteral, subcutaneous, intravenous, intramuscular, or any other path of administration known to the skilled practitioner. The mode of administration, the dose and the number of administrations can be optimized by those skilled in the art in a known manner. However, most commonly a patient is vaccinated with a second administration about one month to six weeks after the first vaccination administration. Third, fourth, and subsequent administrations will most commonly be about one month to six weeks after the previous administration.

The invention provides methods for immunizing an animal body, including a human. In one embodiment a subject mammal, which includes rats, rabbits, mice, and humans are immunized comprising administering a dosage of a recombinant viral vector to the subject, preferably to a human. In one embodiment, the first dosage comprises $10^8$ TCID$_{50}$ of the recombinant virus and the second and additional dosages (i.e., third, fourth, fifth, etc.) comprise $10^8$ TCID$_{50}$ of the virus.

The immunization can be administered either systemically or locally, i.e. parenteral, subcutaneous, intravenous, intramuscular, or any other path of administration known to the skilled practitioner.

In some embodiments, two, three, four, five, six, seven, or more immunizations of a recombinant poxviral vector of the invention can be administered to the host. Preferably, the host is a human.

Immune Responses

Immunizations with the recombinant poxvirus, particularly MVA, of the invention preferably induce strong CD8 T cell responses. The level of CD8 T cell response can be determined by collecting blood from an immunized host and separating peripheral blood mononuclear cells (PBMC). These can be resuspended in growth medium containing 5 μg/ml brefeldin A (BFA, "GolgiPlug", BD Biosciences) with 1 μM of test peptides, including peptides against immunodominant MVA epitopes (i.e., TSYKFESV; SEQ ID NO:9) ("B8R") and peptides derived from the expressed neoantigen. The PBMC can then be incubated for 5 h at 37° C. in 5% CO2, harvested, resuspended in 3 ml cold PBS/10% FCS/2 mM EDTA and stored overnight at 4° C. The following day, the PBMC can be stained with antibodies anti-CD8a-Pac-Blue (clone 53-6.7), anti-CD62L-PE-Cy7, anti-CD44-APCAlexa 750, and anti-CD4-PerCP-Cy5.5 (all antibodies from BD Biosciences). The PBMC can be incubated with appropriate dilutions of the indicated antibodies for 30 min at 4° C. in the dark. After washing, cells can be fixed and permeabilized by using the Cytofix/Cytoperm™ Plus kit (BD Biosciences) according to the manufacturer's instructions. After washing, PBMC can stained for intracellular interferon-γ (IFN-γ) using a FITC-conjugated anti-IFN-γ antibody (BD biosciences) diluted in perm/wash buffer (BD Biosciences). Stained cells can be analysed by flow cytometry.

Antibody responses can be measured by ELISA.

EXAMPLES

Example 1: Generation of MVA Recombinants

The synthetic late/early promoter designated PrA5E contains a late element and five tandemly arranged early promoter elements. The late element was derived from the promoter directing the expression of the A-type inclusion (ATI) protein. The ATI promoter is known to be a relative weak promoter, especially in MVA: see WO 03/097844. The five early elements are all identical and were derived from the immediate early Pr7.5E promoter. They were further optimized according to the consensus sequence for early vaccinia virus promoters. (Broyles, S. S., Vaccinia virus transcription. J. Gen. Virol. 84:2293-2303, 2003; Chakrabarti, S., J. R. Sisler, and B. Moss, Compact, synthetic, vaccinia virus early/late promoter for protein expression. Biotechniques 23:1094-1 097, 1997; Davison and Moss, J. Mol. Biol. 210:749-769, 1989.)

The size of the PrA5E promoter is 230 bp. The sequence is:

```
                                        (SEQ ID NO: 1)
5'gttttgaataaaattttttataataaatatccggtaaaaattgaaaa actattctaatttattgcacggtccggtaaaaattgaaaaactattctaa tttattgcacggtccggtaaaaattgaaaaactattctaatttattgcac ggtccggtaaaaattgaaaaactattctaatttattgcacggtccggtaa aaattgaaaaactattctaatttattgcacgg 3'.
```

The hybrid promoter PrS5E was designed by fusion of the synthetic late+early promoter PrS and 5 repeated core elements coding for the optimized early element of promoter Pr7.5.

The size of the PrS5E promoter is 234 bp. The sequence is:

```
                                        (SEQ ID NO: 2)
5'aaaaattgaaattttatttttttttttggaatataaataaaaaattg aaaaactattctaatttattgcacggtccggtaaaaattgaaaaactatt ctaatttattgcacggtccggtaaaaattgaaaaactattctaatttatt gcacggtccggtaaaaattgaaaaactattctaatttattgcacggtccg gtaaaaattgaaaaactattctaatttattgcacgg 3'.
```

The hybrid promoter Pr4LS5E was designed by fusion of 4 late promoter core elements (PrATI gttttgaataaaattttt-tataataaata, SEQ ID NO:11, PrSSL aatttttaatatataa; SEQ ID NO:14, Pr123L ttctgcataaataaaaatattttttagcttctaaata, SEQ ID NO:15, and Pr124L ttgatcaatagtgaagttattgtcaataaata, SEQ ID NO:16), the synthetic late+early promoter PrS and 5 repeated core elements coding for the optimized early element of promoter Pr7.5.

The size of the Pr4LS5E promoter is 359 bp. The sequence is:

(SEQ ID NO: 3)
5'gttttgaataaaattttttataataaataaattttttaatatataaat attctgcataaataaaatattttagcttctaaatattgatcaatagtg aagttattgtcaataaatagtttaaacaaaaattgaaattttattttttt tttttggaatataaataaaaattgaaaaactattctaatttattgcacg gtccggtaaaaattgaaaaactattctaatttattgcacggtccggtaaa aattgaaaaactattctaatttattgcacggtccggtaaaaattgaaaaa ctattctaatttattgcacggtccggtaaaaattgaaaaactattctaat ttattgcacgg 3'.

The Promoter Pr7.5E opt+spacer was designed using the 34 bp optimized Pr7.5E early element of PrA5E and fusing a 3' terminal 11 bp spacer. The size of the Pr7.5E opt+spacer promoter is 46 bp. The sequence is:

(SEQ ID NO: 4)
5'aaaaattgaaaaactattctaatttattgcacggtccggtgctagc

3'.

The promoter PrSynIIm is a modification of the PrSynII promoter (Wyatt et al 2004). An ATG start codon was destroyed by replacing pos. 58 G→T to avoid additional longer missense proteins. The sequence is:

(SEQ ID NO: 13)
5'taaaaaatgaaaaatattctaatttataggacggttttgattttc ttttttctattctataaataataa 3'

Further 4 nucleotides have been changed to adapt the early promoter part to the early part of Pr7.5: pos. 7 A→T; pos. 15 A→C; pos. 29 A→T; pos. 31 G→C. The size of the promoter PrSynIII is 71 bp. The sequence is:

(SEQ ID NO: 5)
5'taaaaattgaaaaactattctaatttattgcacggttttgattttc ttttttctattctataaataataa 3'.

The promoter MVA50L+PrSSL consists of a native promoter element of the MVA50L gene as identified and defined herein with a fusion of the 16 bp PrSSL promoter. The size of the promoter MVA50L+PrSSL is 57 bp. The sequence is (SEQ ID NO: 6)
5'taaaaaaatcataaaataaattagttttattgctggttgtgaattt ttaatatataa 3'.

The promoter MVA170R+PrSSL consists of a native promoter element of the MVA170R gene with a fusion of the 16 bp PrSSL promoter. The size of the promoter MVA170R+PrSSL is 59 bp. The sequence is:

(SEQ ID NO: 7)
5'aatcaaatcttataccgagtactgtaaaaacaaatttgtacaaat ttttaatatataa 3'.

These promoters were fused directly upstream of the ATG start codon of the open reading frame of chicken ovalbumin (OVA) and the resulting constructs were used to generate the respective recombinant MVA viruses by homologous recombination into intergenic region IGR 44L/45L to obtain MVA constructs expressing OVA under control of the designated promoters. More details of how such constructs can be generated can be taken, for example, from WO 2010/102822. The constructs are depicted in FIG. 1, and were characterized as depicted in FIG. 2.

Example 2: Promoter-Dependent RNA Expression Levels In Vitro

Infection of Hela cells with MVA recombinant viruses at MOI of 10 was done using cold virus attachment on ice for 1 h. After attachment the cells were washed and the zero hour (0 h) time point was collected or cells were incubated at 37° C. for collection of other time points. Samples were collected at 2, 4, 6, 8, and 24 h p.i. Cells were homogenised and total RNA was extracted. The RNA was DNAse digested and cDNA was synthesized using oligo(dT) priming. The resulting cDNA preparations were used as template in a Taqman based qPCR reaction for the simultaneous amplification of OVA and actin cDNA. Samples were run in an AB7500 cycler from Applied Biosystem.

The strength and kinetics of the different promoters included in these studies were compared at the transcriptional level to determine which promoter(s) produced the earliest and/or highest mRNA levels of a transgene in human cells. The mRNA levels of the OVA transgene were determined at several time points after infection with the different recombinant MVA-BN viruses using RT-qPCR for OVA and beta actin (as normalization control). The results are shown in FIGS. 3A and 3B.

Figure 3:
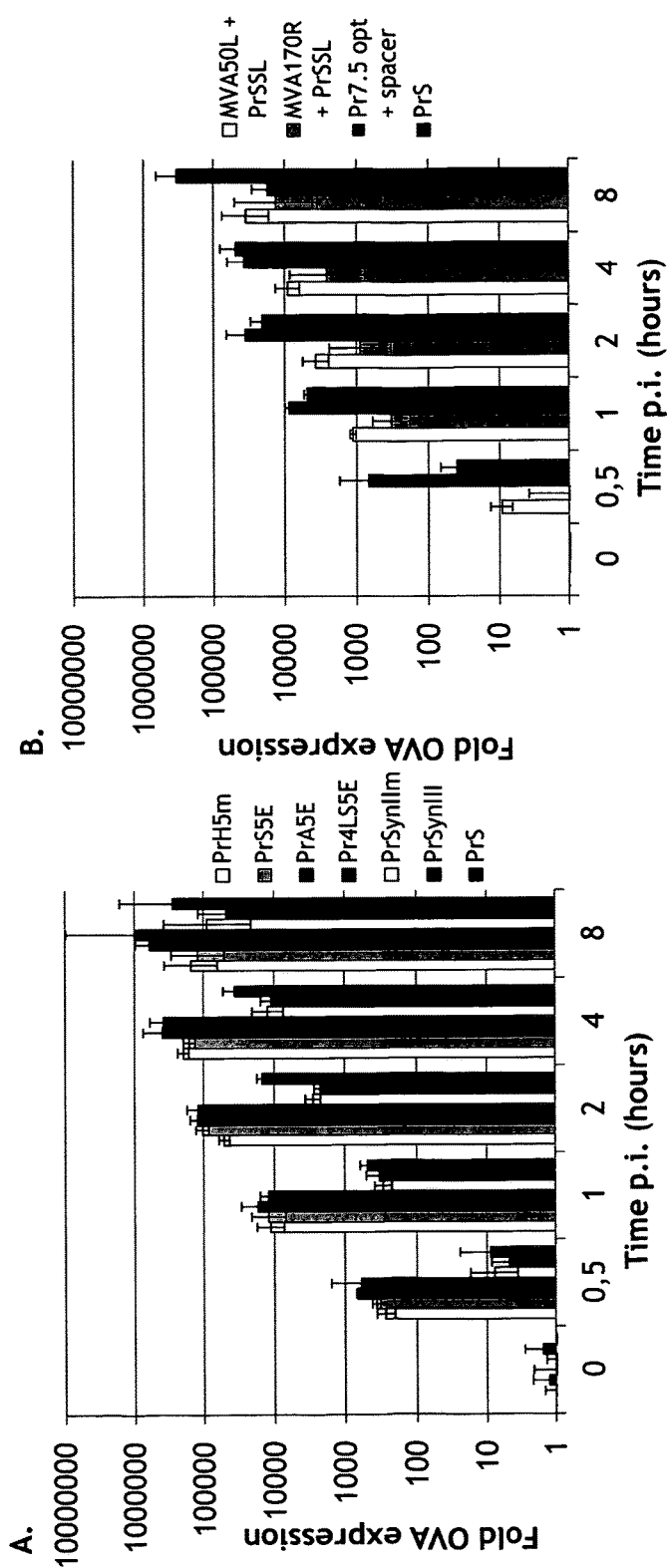
FIGS. 3A and 3B depict kinetics of mRNA expression. OVA mRNA expression levels in infected HeLa cells were determined using RT-qPCR. RNA from infected cells was extracted and cDNA synthesized. Taqman probes specific for OVA mRNA and actin mRNA (as endogenous control) were used to amplify these targets from cDNA in a multiplex qPCR. A) and B) show the OVA mRNA expression levels relative to "empty vector" infected cells at the indicated time points. The ΔΔCT method relative to "empty vector" infected cells (which were arbitrarily assigned a CTOVA=35). All values were normalized to actin levels. The average ΔΔCTs from three independent runs were used to calculate the reported expression levels. Error bars represent ΔΔCT±SEM values.

PrH5m, PrS5E, PrA5E and Pr4LS5E showed earlier kinetics of expression with approximately 300-700 fold OVA expression relative to MVA-BN infected samples as early as 0.5 h p.i., whereas the PrS, PrSynIIm and PrSynIII showed slower kinetics reaching approximately the same levels of expression at 1 h p.i (FIG. 3A). At later time points (8 h p.i.), all viruses showed similar levels of mRNA expression relative to MVA-BN. Pr7.5 opt+spacer also showed earlier kinetics of expression of OVA expression (FIG. 3B).

The strength and kinetics of the different promoters were then compared at the translational level:

Example 3: Promoter-Dependent Protein Expression Levels In Vitro

HeLa cells were cultured in DMEM with 10% FCS. Hela cells were infected with MOI of 10 (10 $TCID_{50}$ per cell) of the recombinant MVA virus. Infected cells were collected at 0.5, 1, 2, 4, and 8 h p.i., fixed and permeabilized. For each sample, half of the cells were stained for OVA protein using a rabbit anti-chicken OVA antibody and the other half were stained for MVA antigens using a rabbit anti-VACV polyclonal antibody. Samples were analyzed using a FACSCalibur flow cytometry analyzer (BD Biosciences) and FlowJo software.

Figure 4:
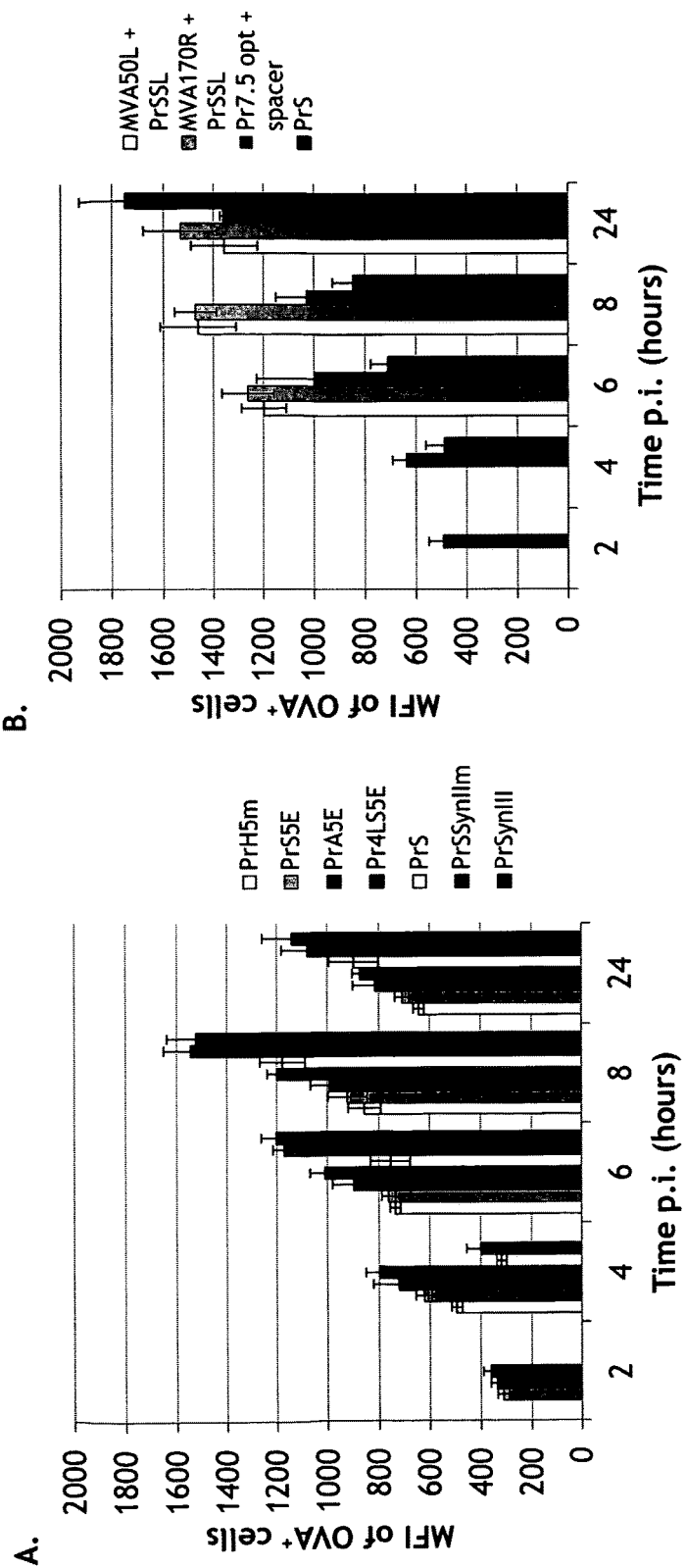
FIGS. 4A and 4B depict kinetics of protein expression. OVA protein expression levels in infected HeLa cells were determined using flow cytometry. Cells were stained for OVA antigen and the percent of OVA positive cells at the indicated times post infection (p.i.) was determined. A) and B) show the mean fluorescence intensity (MFI) of samples with positive OVA staining above background for the indicated promoter constructs obtained from two independent experiments performed in triplicate. Error bars represent ±SEM values.

It was determined which promoter(s) produced the earliest and/or highest protein levels from a transgene in human cells. OVA protein levels expressed by the different recombinant viruses were determined at several time points after infection by staining cells for intracellular OVA protein and MVA antigens (as a control for differences in infection). After the indicated times, infected cells were harvested and analyzed by flow cytometry for MVA and OVA antigens. For data acquisition, uninfected and unstained cells were used to define gates for negative populations. The results are shown in FIGS. 4A and 4B.

Four out of the 5 promoters with strong early transcriptional activity also showed earlier protein kinetics when compared to the PrS promoter, with strong detectable levels of protein as early as 2 h p.i. correlating well with their early transcriptional activity. At 4 h p.i. all 5 promoters with strong early transcriptional activity were still higher than PrS. As expected, the translation efficiency can only be measured at later timepoints than mRNA transcription in qPCR, since after transcription, there is a delay before translation can be done and the detection of low protein amounts by flow cytometry is not as sensitive as for low mRNA amounts in qPCR.

The PrSynIIm, PrSynIII, MVA50L+PrSSL and MVA170R+PrSSL promoters showed later or similar mRNA and protein expression kinetics when compared to the PrS promoter. The protein levels of these were higher than with the PrS promoter at later time points during infection (6-8 h p.i.). These promoters were regarded as having predominantly late activity.

Example 4: Mice Immunizations and Bleeds

Nine groups of 5 mice were used for the study. Each group received a total of three immunizations as depicted in FIG. 2. A PBS-injected group served as a control for immune responses. Blood was taken via the tail vein for analysis of immune responses throughout the study.

Mice were immunized i.p. with $10^8$ TCID$_{50}$ of the respective MVA viruses diluted in PBS (300 µL, total volume) at weeks 0, 4 and 8. Bleeds for T cell analysis were performed one week after each immunization and bleeds for antibody analysis were performed three weeks after each immunization.

Mice were immunized at time 0 and at 4 and 8 weeks with recombinant MVA viruses expressing OVA under the control of different promoters, with empty vector, or with PBS. Blood was taken 1 week after each immunization (weeks 1, 5, and 9) for determination of T cell responses.

Example 5: T Cell Staining and Antibody Detection

Figure 5:
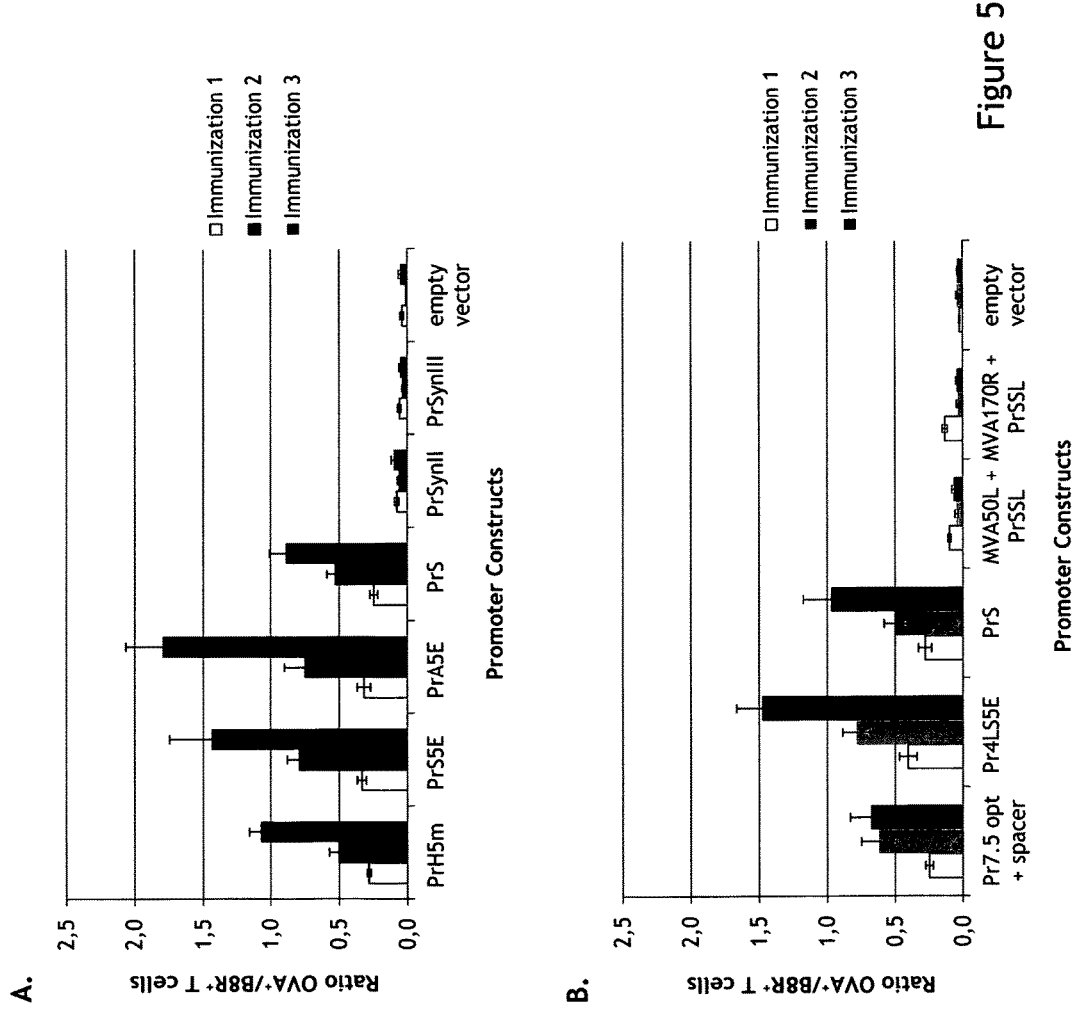
FIGS. 5A and 5B depict CD8 T cell responses. OVA and vector specific CD8 T cells from immunized mice were stained using MHC class I dextramers complexed with the H-2Kb binding peptide SIINFEKL (an OVA epitope; SEQ ID NO:8) or TSYKFESV (an MVA-vector, B8R, epitope; SEQ ID NO:9), respectively. The percentages of OVA and B8R specific CD8 T cells were used to calculate OVA-to-B8R ratios for individual mice. Ratios reported are the arithmetic mean for each group. Error bars represent ±SEM. All groups consisted of 4-5 mice. A and B show the results for the indicated promoter constructs after 1, 2, and 3 administrations obtained from two independent animal experiments in which the PrS promoter and the "empty vector" groups served as controls. Ratios above 1 indicate immunodominance of the OVA epitope over the MVA vector derived B8R epitope.

Approximately 100-120 µl of blood per mouse was collected in FACS/heparin buffer. PBMCs were prepared by lysing erythrocytes with RBC lysis buffer. PBMCs were then co-stained in a single reaction for OVA- and B8R-specific CD8 T cells using an anti-CD8a-FITC, CD44-PerCPCy5.5 and MHC class I dextramers complexed with their respective H-2Kb binding peptides, SIINFEKL (SEQ ID NO:8) or TSYKFESV (SEQ ID NO:9). The MHC class I SIINFEKL-dextramer (SEQ ID NO:8) was labelled with PE and the TSYKFESV-dextramer (SEQ ID NO:9) with APC. Stained cells were analyzed by flow cytometry on a BD Biosciences BD LSR II system. Ten thousand CD8+ T cells were acquired per sample. The results are shown in FIG. 5.

Figure 6:
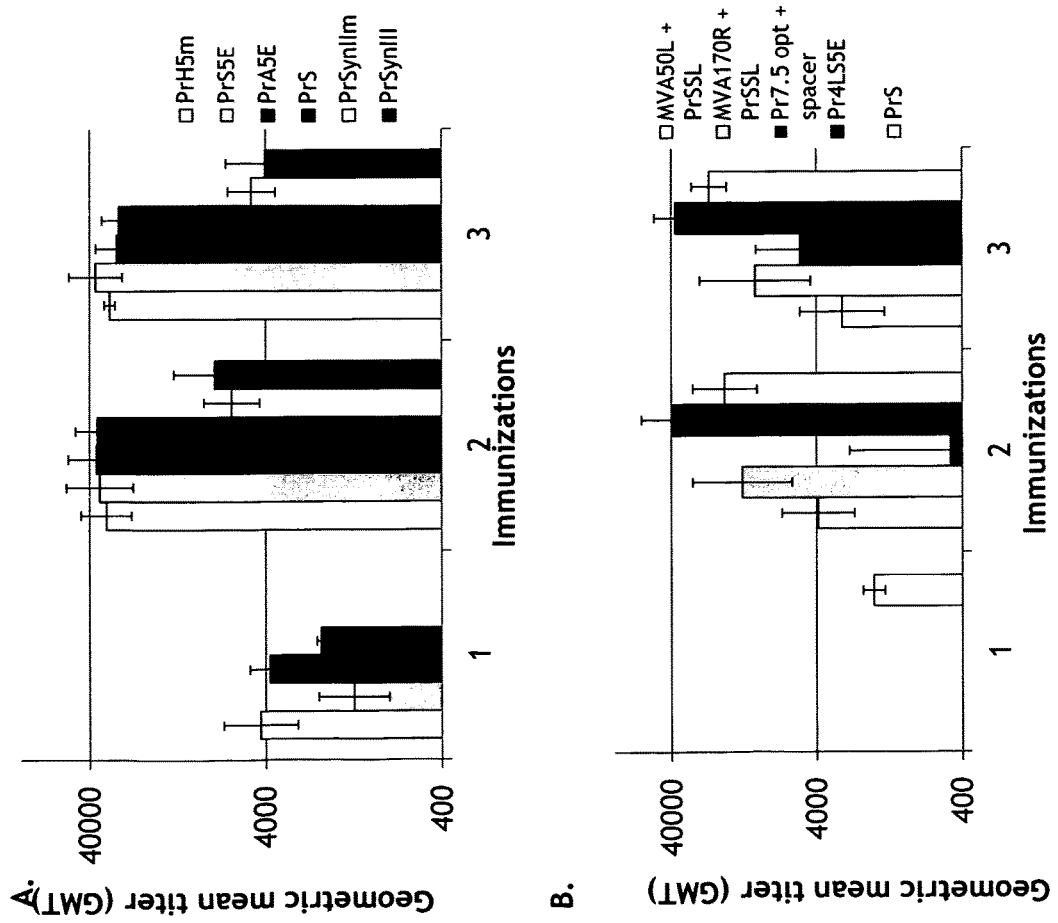
FIGS. 6A and 6B depict antibody responses. OVA-specific antibody end-point titers were calculated for all mice and the geometric mean titer (GMT) for each group was calculated. GMT values <400 were considered below quantification limits. Upper and lower error bar values were calculated from log transformed values ±SEM. All groups consisted of 4-5 mice. A and B show the results for the indicated promoter constructs obtained after 1, 2, and 3 administrations from two independent animal experiments in which the PrS promoter served as control. No OVA-specific titers were detected for "empty vector" or PBS control groups.

Serum from whole blood was prepared. Ovalbumin ELISA and MVA ELISA were performed to detect specific antibodies. The results are shown in FIG. 6.

The invention claimed is:

1. An early/late hybrid promoter comprising (a) a late element driving late expression of an antigenic determinant and (b) at least two Pr7.5 early elements (Pr7.5E) driving early expression of the antigenic determinant, wherein the late element is linked to the at least two early elements, and wherein RNA levels from the late element in a recombinant modified vaccinia Ankara (MVA) virus are at least 1.5 fold greater than RNA levels produced by the SEQ ID NO: 11 promoter in a recombinant MVA virus in HeLa cells.

2. The promoter of claim 1, wherein the promoter is a poxviral promoter.

3. The promoter of claim 1, wherein the late element comprises one or more elements selected from the group consisting of SEQ ID NO: 10, SEQ ID NO: 14, SEQ ID NO: 15, and SEQ ID NO: 16.

4. The promoter of claim 1, wherein the Pr7.5E is optimized (Pr7.5E opt).

5. The promoter of claim 4, wherein the Pr7.5E opt comprises SEQ ID NO:4.

6. The promoter of claim 4, wherein the Pr7.5E opt comprises nucleotides (nt) selected from nt 1-34 or nt 17-34 of SEQ ID NO:4.

7. The promoter of claim 4, wherein the Pr7.5E is fused to a 3' spacer of at least 3 bp.

8. The promoter of claim 7, wherein the 3' space comprises nucleotides 35-46 of SEQ ID NO:4.

9. The promoter of claim 1, wherein the promoter comprises at least five copies of the Pr7.5 early elements.

10. The promoter of claim 1, wherein the promoter comprises the nucleotide sequence of SEQ ID NO:2 or SEQ ID NO:3.

11. A recombinant poxviral vector comprising the promoter of claim 1.

12. The recombinant poxviral vector of claim 11, wherein the poxviral vector is selected from Vaccinia Virus (VV), Modified Vaccinia Ankara (MVA) virus, or Modified Vaccinia Ankara-Bavarian Nordic (MVA-BN).

13. A pharmaceutical composition or compound comprising the promoter of claim 1.

14. A method for affecting an immune response in a human without raising a strong antibody response after a first, priming immunization, the method comprising administering to the human a recombinant poxviral vector comprising an early/late hybrid promoter comprising:
  a. a late element driving late expression of an antigenic determinant; and
  b. at least two Pr7.5 early elements (Pr7.5E) driving early expression of the antigenic determinant;
  c. wherein the late element is linked to the at least two Pr7.5E elements; and
  d. wherein RNA levels from the late element in a recombinant modified vaccinia Ankara (MVA) virus are at least 1.5 fold greater than RNA levels produced by the SEQ ID NO: 11 promoter in a recombinant MVA virus in HeLa cells.

15. The method of claim 14, wherein after the first, priming immunization a CD8 T-cell response is induced.

16. The method of claim 14, wherein the promoter comprises the nucleotide sequence of SEQ ID NO:2, SEQ ID NO:3, or SEQ ID NO:4.

17. The method of claim 14, wherein the promoter comprises the nucleotide sequence of SEQ ID NO:4.

* * * * *

SEQUENCE LISTING

```
<160> NUMBER OF SEQ ID NOS: 16

<210> SEQ ID NO 1
<211> LENGTH: 230
<212> TYPE: DNA
<213> ORGANISM: Artificial
<220> FEATURE:
<223> OTHER INFORMATION: PrA5E promoter

<400> SEQUENCE: 1
gttttgaata aaattttttt ataataaata tccggtaaaa attgaaaaac tattctaatt      60
tattgcacgg tccggtaaaa attgaaaaac tattctaatt tattgcacgg tccggtaaaa     120
attgaaaaac tattctaatt tattgcacgg tccggtaaaa attgaaaaac tattctaatt     180
tattgcacgg tccggtaaaa attgaaaaac tattctaatt tattgcacgg                230

<210> SEQ ID NO 2
<211> LENGTH: 234
<212> TYPE: DNA
<213> ORGANISM: Artificial
<220> FEATURE:
<223> OTHER INFORMATION: PrS5E promoter

<400> SEQUENCE: 2
aaaaattgaa attttatttt ttttttttgg aatataaata aaaaattgaa aaactattct      60
aatttattgc acggtccggt aaaaattgaa aaactattct aatttattgc acggtccggt     120
aaaaattgaa aaactattct aatttattgc acggtccggt aaaaattgaa aaactattct     180
aatttattgc acggtccggt aaaaattgaa aaactattct aatttattgc acgg           234

<210> SEQ ID NO 3
<211> LENGTH: 359
```

```
<212> TYPE: DNA
<213> ORGANISM: Artificial
<220> FEATURE:
<223> OTHER INFORMATION: Pr4LS5E promoter

<400> SEQUENCE: 3
gttttgaata aaattttttt ataataaata aatttttaat atataaatat tctgcataaa      60
taaaaatatt tttagcttct aaatattgat caatagtgaa gttattgtca ataaatagtt     120
taaacaaaaa ttgaattttt attttttttt tttggaatat aaataaaaaa ttgaaaaact     180
attctaattt attgcacggt ccggtaaaaa ttgaaaaact attctaattt attgcacggt     240
ccggtaaaaa ttgaaaaact attctaattt attgcacggt ccggtaaaaa ttgaaaaact     300
attctaattt attgcacggt ccggtaaaaa ttgaaaaact attctaattt attgcacgg     359

<210> SEQ ID NO 4
<211> LENGTH: 46
<212> TYPE: DNA
<213> ORGANISM: Artificial
<220> FEATURE:
<223> OTHER INFORMATION: Pr7.Eopt+spacer promoter

<400> SEQUENCE: 4
aaaaattgaa aaactattct aatttattgc acggtccggt gctagc                    46

<210> SEQ ID NO 5
<211> LENGTH: 71
<212> TYPE: DNA
<213> ORGANISM: Artificial
<220> FEATURE:
<223> OTHER INFORMATION: PrSynIII promoter

<400> SEQUENCE: 5
taaaaattga aaactattc taatttattg cacggttttg attttctttt tttctattct       60
ataaataata a                                                          71

<210> SEQ ID NO 6
<211> LENGTH: 57
<212> TYPE: DNA
<213> ORGANISM: Artificial
<220> FEATURE:
<223> OTHER INFORMATION: MVA50L+PrSSL promoter

<400> SEQUENCE: 6
taaaaaaatc ataaaataaa ttagttttat tgctggttgt gaattttaa tatataa          57

<210> SEQ ID NO 7
<211> LENGTH: 59
<212> TYPE: DNA
<213> ORGANISM: Artificial
<220> FEATURE:
<223> OTHER INFORMATION: MVA170R+PrSSL promoter

<400> SEQUENCE: 7
aatcaaaatc ttataccgag tactgtaaaa acaaatttgt acaattttt aatatataa        59

<210> SEQ ID NO 8
<211> LENGTH: 8
<212> TYPE: PRT
<213> ORGANISM: Artificial
<220> FEATURE:
<223> OTHER INFORMATION: H-2Kb binding OVA-derived peptide

<400> SEQUENCE: 8
```

Ser Ile Ile Asn Phe Glu Lys Leu
1               5

<210> SEQ ID NO 9
<211> LENGTH: 8
<212> TYPE: PRT
<213> ORGANISM: Artificial
<220> FEATURE:
<223> OTHER INFORMATION: H-2Kb binding B8R epitope

<400> SEQUENCE: 9

Thr Ser Tyr Lys Phe Glu Ser Val
1               5

<210> SEQ ID NO 10
<211> LENGTH: 40
<212> TYPE: DNA
<213> ORGANISM: Artificial
<220> FEATURE:
<223> OTHER INFORMATION: PrS promoter

<400> SEQUENCE: 10
aaaaattgaa attttatttt ttttttttgg aatataaata                40

<210> SEQ ID NO 11
<211> LENGTH: 30
<212> TYPE: DNA
<213> ORGANISM: Artificial
<220> FEATURE:
<223> OTHER INFORMATION: Cowpox ATI promoter

<400> SEQUENCE: 11
gttttgaata aaatttttt ataataaata                            30

<210> SEQ ID NO 12
<211> LENGTH: 34
<212> TYPE: DNA
<213> ORGANISM: Artificial
<220> FEATURE:
<223> OTHER INFORMATION: Pr/.5Eopt promoter elemen

<400> SEQUENCE: 12
aaaaattgaa aaactattct aatttattgc acgg                      34

<210> SEQ ID NO 13
<211> LENGTH: 71
<212> TYPE: DNA
<213> ORGANISM: Artificial
<220> FEATURE:
<223> OTHER INFORMATION: PrSynIIm promoter

<400> SEQUENCE: 13
taaaaaatga aaaaatattc taatttatag gacggttttg attttctttt tttctattct    60
ataaataata a                                               71

<210> SEQ ID NO 14
<211> LENGTH: 16
<212> TYPE: DNA
<213> ORGANISM: Artificial
<220> FEATURE:
<223> OTHER INFORMATION: PrSSL promoter

<400> SEQUENCE: 14 aattttaat atataa                                           16

```
<210> SEQ ID NO 15
<211> LENGTH: 36
<212> TYPE: DNA
<213> ORGANISM: Artificial
<220> FEATURE:
<223> OTHER INFORMATION: Pr123L promoter

<400> SEQUENCE: 15
ttctgcataa ataaaaatat ttttagcttc taaata                                36

<210> SEQ ID NO 16
<211> LENGTH: 32
<212> TYPE: DNA
<213> ORGANISM: Artificial
<220> FEATURE:
<223> OTHER INFORMATION: Pr124L promoter

<400> SEQUENCE: 16
ttgatcaata gtgaagttat tgtcaataaa ta                                    32
```